(12) United States Patent
Henderson

(10) Patent No.: US 6,228,265 B1
(45) Date of Patent: May 8, 2001

(54) BIO-ENHANCER

(75) Inventor: Garth M. Henderson, Olds (CA)

(73) Assignee: Digestco Limited, Alberta (CA)

( * ) Notice: Subject to any disclaimer, the term of this patent is extended or adjusted under 35 U.S.C. 154(b) by 0 days.

(21) Appl. No.: 09/101,352

(22) PCT Filed: Jan. 10, 1997

(86) PCT No.: PCT/IB97/00010

§ 371 Date: May 7, 1999

§ 102(e) Date: May 7, 1999

(87) PCT Pub. No.: WO97/25411

PCT Pub. Date: Jul. 17, 1997

(30) Foreign Application Priority Data

Jan. 11, 1996 (CA) .................................................. 9600517

(51) Int. Cl.$^7$ .................................................. C02F 3/00
(52) U.S. Cl. .................................................. 210/610
(58) Field of Search .................................. 210/610, 611

(56) References Cited

U.S. PATENT DOCUMENTS 4,927,530 * 5/1990 Ueda .................................. 210/149
4,986,994 * 1/1991 Baccus .............................. 426/330.3
5,081,033   1/1992 Dorn et al. ........................... 435/244
5,639,794 * 6/1997 Emerson et al. ..................... 514/699
5,792,467 * 8/1998 Emerson et al. ..................... 424/405
5,895,680 * 4/1999 Cirigliano ............................ 426/326

FOREIGN PATENT DOCUMENTS 0 063 621   11/1982 (EP) .
0 268 575    5/1988 (EP) .
61 118 189   6/1986 (JP) .
63 242 400  10/1988 (JP) .

OTHER PUBLICATIONS

Grant & Hackh's Chemical Dictionary, 5th edition, 1987, "Brix degree," p. 95.*

* cited by examiner

Primary Examiner—Chester T. Barry
(74) Attorney, Agent, or Firm—Seed IP Law Group PLLC

(57) ABSTRACT

There is disclosed a bio-enhancing composition comprising a carbohydrate and saponin, preferably comprising yucca extract, for the acceleration of bacterial metabolism. This particularly useful in the acceleration of bacterial metabolism in the breakdown of organic waste. There is also provided a method of stimulating microorganism metabolism and the use of the composition for such stimulation.

7 Claims, 4 Drawing Sheets

BIO-ENHANCER

Figure 1:
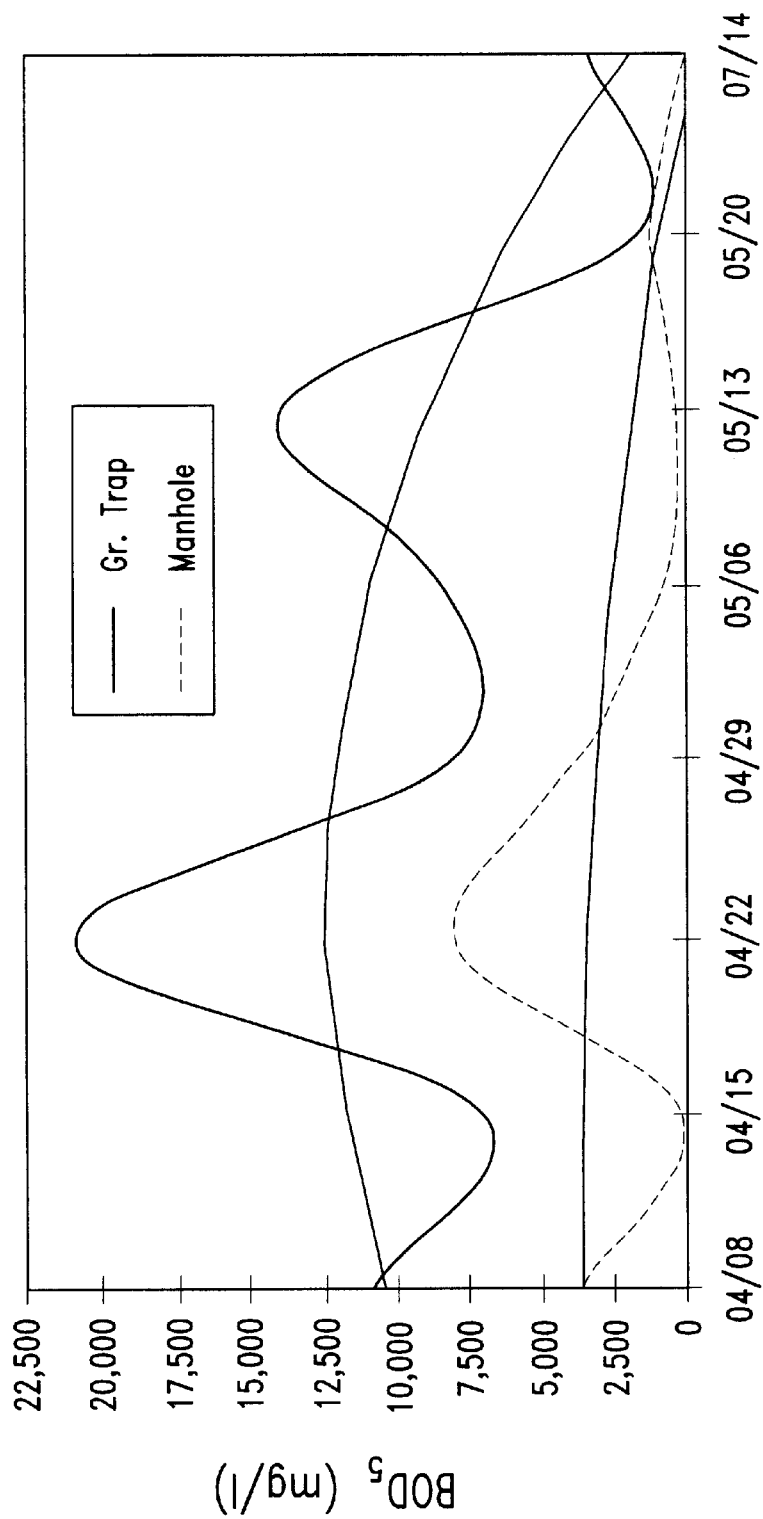

The present invention relates to a bio-enhancer and more particularly a natural bio-enhancer for accelerating microbial metabolism.

In recent years the increased production and subsequent removal of waste products has become of increasing concern, particularly with regard to the damage caused to the environment both by the waste products and by attempts to dispose of them. Whilst much attention has been focused on waste products from industry such as chemical plants and oil fields, increased production of more domestic waste products, such as sewage and food, both from homes and catering establishments is also becoming a problem.

Increased production of waste products such as grease and sewage has led to several problems in various areas of the world. Such problems are the clogging of waste pipes causing such pipes to back up dangerously, the increase in noxious odours from the waste outlets and build-up of potentially dangerous materials in collecting areas such as grease traps and sewage holding tanks. There is a constant need for new means for solving, or at least easing, such problems in a way that is not harmful to the environment.

According to the present invention there is provided a bio-enhancing composition for stimulating the metabolism of a microorganism which composition comprises carbohydrate and at least 0.01% by weight of saponin. Preferably the composition comprises yucca extract.

It is preferred that the composition has a Brix value of approximately 5 to 30, preferably 10 to 20 and more preferably 15 to 18. It is particularly preferred that yucca extract is obtained from the schidigera species of yucca. In a specific embodiment of the present invention the composition is used to accelerate bacterial metabolism and preferably to accelerate bacterial metabolism in the degradation of organic waste.

In another aspect of the present invention there is provided a method of stimulating the metabolism of a microorganism comprising contacting the microorganism with a composition according to the present invention.

According to a third aspect of the present invention, there is provided the use of a bio-enhancing composition according to the present invention for the stimulation of a metabolism of a microorganism.

Yucca extract, as used in the present invention, is produced by pressing the trunk of a yucca plant. The liquid obtained directly from this pressing may be used, unchanged, in the present invention. The sugar values of the extract depend on the time of year of harvest of the plant. In the spring or wet season the sugar value is low whilst in the autumn or dry season, the sugar value is high. Yucca extracts taken at different times of the year may be blended to give any specific Brix value.

It is particularly preferred that the species from which the yucca extract is obtained is the yucca schidigera.

The composition of the present invention may be used to accelerate the metabolism of all microorganisms, notably bacteria. It may be used not only in the acceleration of bacterial metabolism in degradation of organic waste products but also in the acceleration of bacterial metabolism used to degrade oil spills, in recycling plants, or in various biotechnological applications. Other possible uses are in composts, in the increased bacterial/microbial activity of contaminated soils, and in other environments which require increased bacterial activity such as golf course turf, farmland, farmwater, ponds, water hazards and potable water.

It is preferred that the yucca extract is not diluted so much as to take the Brix value below 5 or concentrated so much as to take the Brix value above 30. It is particularly preferred that the Brix value be maintained between 10 and 20 brix and the best results have been obtained with a Brix value of between 15 and 18.

It is thought that the saponin present in yucca, combined with the relatively high Brix value, may be the cause of the bacterial acceleration. Certainly the extracts from other plants containing saponin, such as oranges, have been found to be ineffective as bacterial accelerants.

It has been found that the composition of the present invention increases the respiration of the bacteria, causing increased carbon dioxide production. This in turn allows bacteria to break down organic waste more quickly and efficiently. A phenomenon that is observed as a result of such an acceleration in the bacterial metabolism is that, in the absence of oxygen, treated liquid containing organic waste shows a marked reduction in pH with time but that, in the presence of oxygen, a similarly treated liquid will show an increase in pH with time, in the presence of the composition of the present invention. This is explained by the fact that, in anaerobic conditions, bacteria produce volatile fatty acids, lowering the pH whilst, in the presence of oxygen, bacteria actually consume such volatile fatty acids as energy sources, so as to increase the pH.

A preferred dosage is one part per million of yucca extract per volume of treated sample.

The present invention will now be further described, by way of example only, with reference to the following examples.

In the following examples, the yucca extract used was tested and shown to have the composition:

Lab Testing for Contents of Yucca Extract

| TEST | METHOD | RESULT |
| --- | --- | --- |
| FAT | AOAC 950.54 | 0.2% |
| PROTEIN (N × 6.25) | AOAC 992.23 | 0.8% |
| ENERGY | Atwater Method, USDA Handbook 74 | 43 Kilo-cals/100 g |
| CARBOHYDRATES | Atwater Method USDA Handbook 74 | 9.6% |
| SAPONIFICATION VALUE | AOCS Cd 3-25 | 30.9% |
| SUCROSE | AOAC 971.18 | 0.1% |
| FRUCTOSE | AOAC 971.18 | 2.2% |
| ALPHA-GLUCOSE | AOAC 971.18 | 1.4% |
| BETA-GLUCOSE | AOAC 971.18 | 0.6% |
| LACTOSE | AOAC 971.18 | <0.1% |
| TOTAL SUGARS | AOAC 971.18 | 4.3% |

The above lab test results can vary from sample to sample according to plant, growing area and growing conditions in the growing area. Because of the variances of the plants, these results should be taken as guide lines only.

EXAMPLE 1

The yucca extract was used in a busy restaurant for a period of three months. The correct dose of 4 oz was poured into a sink near a grease trap, by a metering pump in doses of 0.5 ounces per application, using 8 applications, evenly spread, for timing per day.

FIG. 1 shows the $BOD_5$ results taken from both the grease trap of the restaurant and a manhole outside the restaurant thus monitoring the sewage coming from the restaurant. $BOD_5$ is the biochemical oxygen demand over five days. It is a measure of the reduction of dissolved oxygen in a specific example of organic material over a five day period. A high figure indicates a great deal of undigested organic material in the sample tested.

Figure 2:
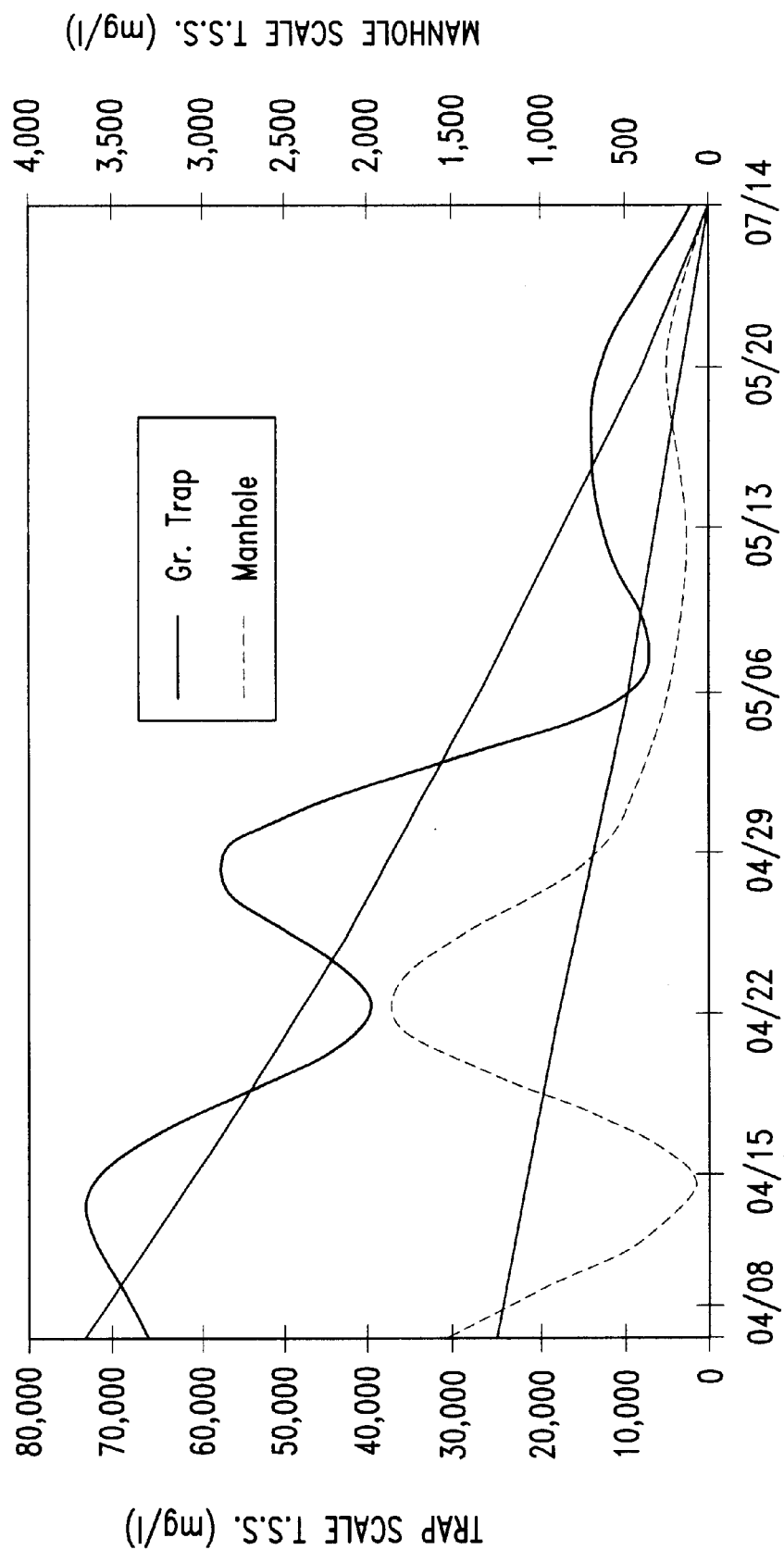

FIG. 2 shows the total suspended solids in samples taken from both the grease trap and the outside manhole over the same three month period.

Both $BOD_5$ and total suspended solids were reduced significantly. This could only have taken place as a result of an increase in the digestion rate of organic waste in the grease trap and in the sewer service line leaving the restaurant. The reduction of total suspended solids indicates that the digestion process was accelerated so as to remove suspended organic material from the effluent whilst the reduction in $BOD_5$ indicates a reduced need for oxygen to support the secondary digestion activities of aerobic and facultative bacteria as a result of the greatly reduced volume of undigested organic waste in the affluent.

As can be seen from the results, the amount of organic waste reaching both the grease trap and the sewer line decreased over the three month period that the composition according to the present invention was applied to the sink. The results showed a 98% reduction in suspended solids in both the grease trap and the manhole whilst the oxygen demand was reduced by 71% in the grease trap and 99% in the manhole, thereby showing an extremely efficient degradation of the organic waste.

The noxious odours emitted from the grease trap and the manhole were substantially eliminated, thus benefiting both customers and staff of the restaurant. In this respect, the toxic fume production producing such noxious odours is reduced by the digestion of volatile fatty acids by the bacteria, accelerated by the composition of the present invention.

The compositions according to the present invention, when used regularly, clearly accelerate the breakdown of organic waste, not only in the environment immediately surrounding the restaurant, such as in grease traps, but also in the sewer lines leading from the environments in which the composition is used. This causes acceleration of natural biodegradation of organic waste in the various sewerage pipes leading from that environment, greatly reducing the build-up of such waste, combined with larger bodies, in the sewage pipes so as to reduce or eliminating clogging and damming of the pipes and thus backup of the pipe.

The compositions of the present invention act on all naturally occurring bacteria that feed on organic waste and are effective in the presence of a variety of foodstuffs such as produce, beans and dough as well as grease. A further secondary advantage is that the increase in bacterial activity will increase the degradation of organic waste adhering to the inside of pipes carrying such waste thereby practically widening the passage through which such waste may pass enabling loading peaks to pass through the system more readily.

EXAMPLE 2

The composition according to the present invention was used in the treatment of waste water in a sewage main to ascertain the effectiveness of the composition according to the present invention of the degradation of a wider variety of organic waste. The main chosen for this test ran for 27.5 kilometers in a combination of force and gravity mains. The force main accounted for 12.5 kilometers and there were three pumping stations with wet wells. There was also a large sewage tank and other holding tanks from businesses pumped into the sewage main. The combination of these factors are ideal for anaerobic conditions leading to high gas production and high $BOD_5$ causing serious problems in the management of such organic waste.

In this respect, a great deal of $H_2S$ gas was entering the headworks of the waste water treatment plant. The gas was making the atmosphere very acidic and causing extreme problems with the electronic circuitry in the plant control systems leading to failure of the system. The composition of the present invention was added at the head of the sewer main running to the waste water treatment plant headworks at the lift station which was at the beginning of the line at a daily addition.

The main was treated with a composition according to the present invention in daily doses of one part per million composition per volume of effluent. The idea was to increase aerobic and facultative digestion so as to reduce the amount of $H_2S$ arriving at the plant works which $H_2S$ was highly corrosive and caused a great deal of problems. Weekly samples of the material passing through the regional through a pipeline were taken between 1st December and 24th March. The application of the composition according to the present invention commenced on 12th January and finished on 17th March. The results are shown in Table 1.

TABLE 1

WASTE WATER PIPE ANALYSIS
Treatment of regional sewer pipeline:
Start Jan 12: Stop Mar. 17
($BOD_5$, TSS and $H_2S$ results are mg/l)

| | pH | $BOD_5$ | TSS | $H_2S$ |
|---|---|---|---|---|
| Dec. 1 | 7.83 | 127 | 64 | 2.00 |
| Dec. 8 | 7.79 | 103 | 78 | 1.00 |
| Dec. 15 | 7.71 | 86 | 40 | 2.00 |
| Dec. 22 | 7.81 | 103 | 96 | 0.80 |
| Dec. 29 | 7.84 | 155 | 66 | 3.50 |
| Jan. 5 | 7.79 | 132 | 68 | 0.30 |
| Jan. 12 | 7.77 | 85 | 64 | 0.20 |
| Jan. 19 | 7.74 | 63 | 80 | 0.70 |
| Jan. 29 | 7.76 | 79 | 46 | 0.50 |
| Feb. 2 | 7.69 | 97 | 34 | 0.00 |
| Feb. 16 | 7.75 | 93 | 64 | 0.05 |
| Feb. 23 | 7.73 | 67 | 66 | 0.60 |
| Mar. 3 | 7.72 | 103 | 54 | 0.60 |
| Mar. 10 | 7.88 | 126 | 74 | 0.70 |
| Mar. 17 | 7.75 | 117 | 48 | 0.00 |
| Mar. 24 | 7.74 | 86 | 64 | 0.80 |

Figure 3:
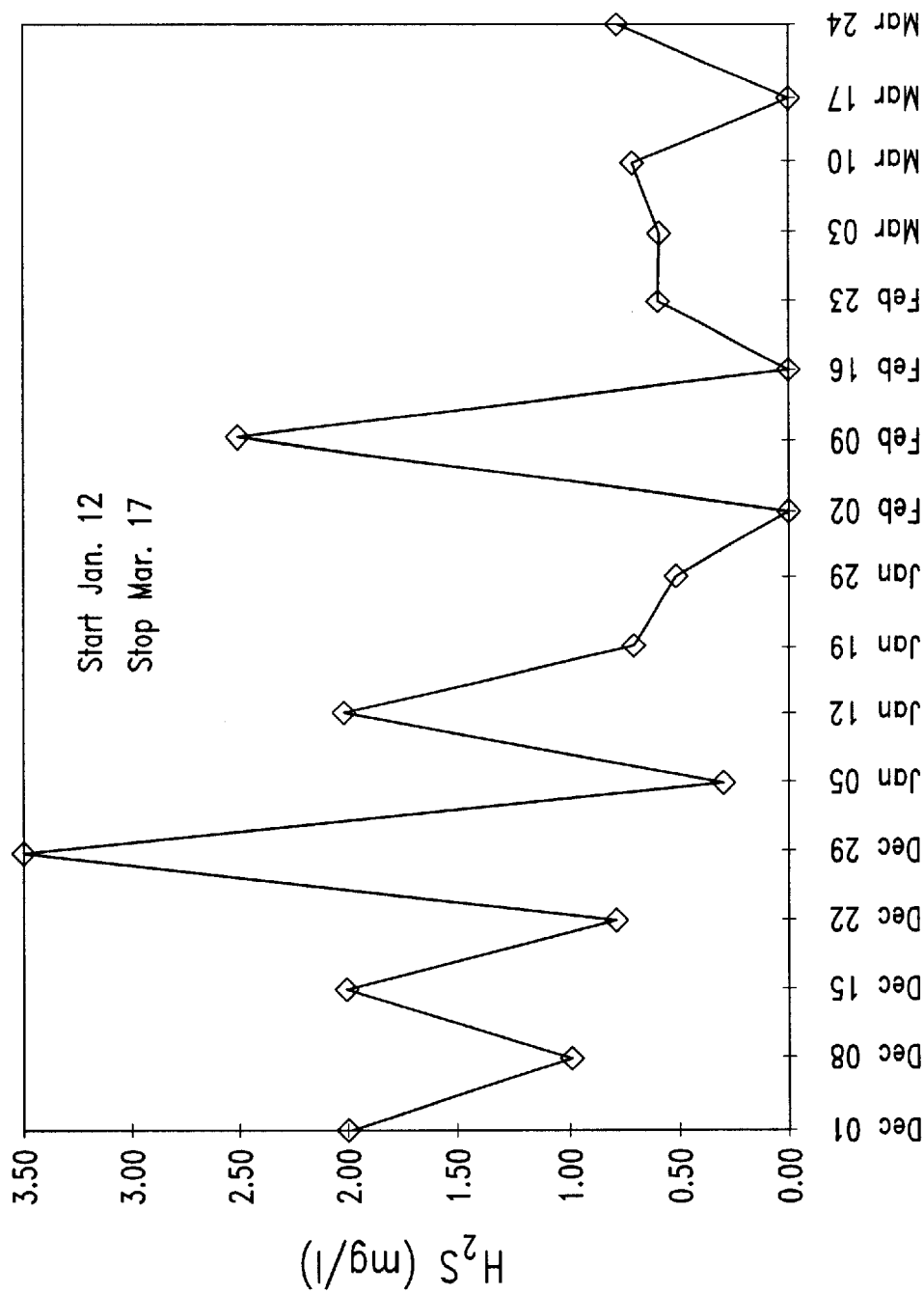

As can be seen from the table, whilst the pH remained relatively constant, there was a general decrease in $BOD_5$ and in total suspended solids (TSS) and a significant decrease in $H_2S$ production. FIG. 3 clearly displays the changes in soluble $H_2S$ content over the test period showing the decrease in $H_2S$ levels. The average level of soluble $H_2S$ before treatment was 1.40 mg/l whilst the average level during treatment was 0.64 mg/l showing a reduction of 54%.

The initial $BOD_5$ demand was relatively low for raw sewage before treatment. However, the average $BOD_5$ before treatment was 113 mg/l and was reduced, during treatment, to 94 mg/l, a somewhat surprising 17% reduction given the extremely low figure to start with. The apparent increase in both $BOD_5$ and $H_2S$ figures around the beginning of March coincided with the pumping out of the sewage holding tank thereby increasing the loading on the system.

Digestion of $H_2S$ is a function of secondary digestion of organics waste performed by aerobic and facultative bacteria. Therefore the significant reduction of $H_2S$ amounts showed the increase in digestion rate by such bacteria, clearly caused by the addition of the compositions of the present invention.

It is clear that the compositions of the present invention, by accelerating bacterial metabolism, caused increased degradation of sewage and reduce the production of corrosive byproducts, notably $H_2S$. Those mains that suffer from $H_2S$ production as a result of shallow grade and very slow flow would also benefit from the addition of compositions according to the present invention. Bacterial action, duly accelerated will help to suspend collected solids in the main and, by removing solids from the relative section of pipe, the gas production from the stranded solids will be controlled.

EXAMPLE 3

One method of digesting organics in sewage or waste water is the use of aerated cells. An aerated cell is a tank or cell that has compressed air blown into the sample located in the cell so as to increase the dissolved oxygen content, aiding the digestion of the sewage in an aerobic manner. This method, although more expensive than the more traditional anaerobic method, has the advantage that the digestion process is accelerated and odours are reduced.

In the present example the composition of the present invention was used during the spring flushing of the sewer mains into the aerated cells. Cell 1, the main aerated cell, receives an increase of solids which normally causes an increase in $BOD_5$ of the effluent passing between the cells thereby causing a major increase in odours spreads into the surrounding community causing great distress. The flushing process can take several days. However, a suggested dosage amd timing would be 0.2 parts per million over a 24 hour period.

Figure 4:
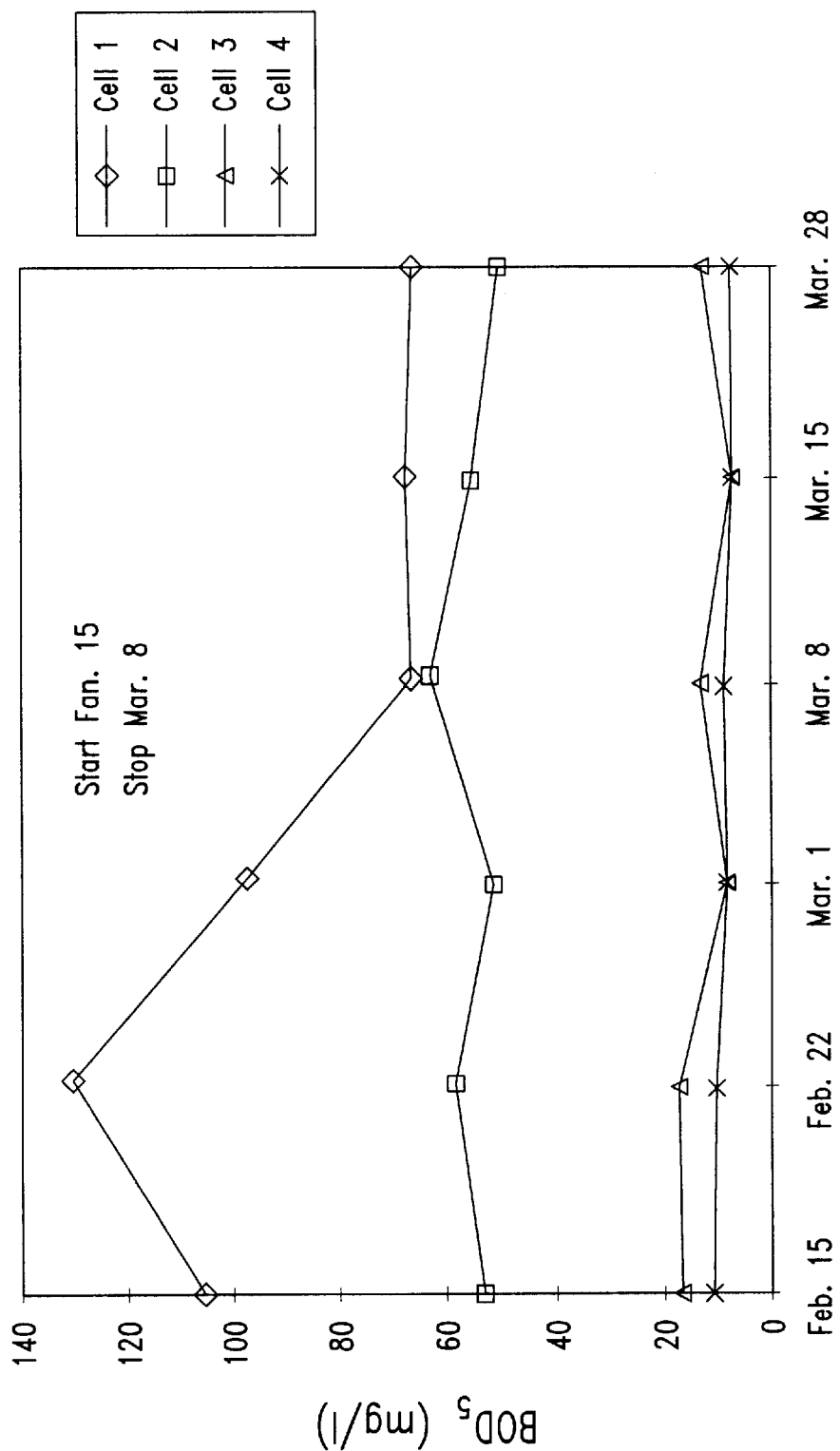

Four aerated cells were treated for a period of five weeks with the yucca extract composition of the present invention. Table 2 shows the data collected for each cell in respect of the $BOD_5$ of all cells. A plot of these results is shown in FIG. 4.

TABLE 2

AERATED CELLS TREATMENT
Start Feb. 15; Stop Mar. 8
($BOD_5$ RESULTS are mg/l)

|  | Cell 1 | Cell 2 | Cell 3 | Cell 4 |
| --- | --- | --- | --- | --- |
| Feb. 15 | 105 | 54 | 17 | 11 |
| Feb. 22 | 128 | 59 | 18 | 11 |
| Mar. 1 | 98 | 53 | 10 | 9 |
| Mar. 8 | 68 | 65 | 14 | 11 |
| Mar. 15 | 69 | 57 | 9 | 9 |
| Mar. 28 | 69 | 53 | 14 | 10 |

Whilst cell 1 showed a clear reduction in $BOD_5$ the results for cells 2 to 4 are slightly more ambiguous.

It was found that, in cell 4, a great deal of algae bloomed. The extract of the present invention was used to attempt to increase the digestion rate in that cell given the large amount of algae. Whilst the amount of algae proved too much to deal with the $BOD_5$ was controlled to near 30 mg/l without any improvement. It seems that, in order to control algae, immediate action is needed at the first signs of an outbreak so as to reduce the organic content and control the $BOD_5$.

The huge reduction in $BOD_5$ in cell 1 was thought to be because cell 1 appeared to be near its design capacity whilst the other three cells were operating well within their capacity and, therefore, appear to be operating at a maximum efficiency.

It has also been found that it is best to apply the compositions of the present invention prior to mains flushing so as to reduce foaming problems on the surface of the cells and to control the $BOD_5$ levels at that time.

The decrease in $BOD_5$ shows the ability of the composition to the present invention to increase digestion rates. This allowed the odours from the cells to be kept under control during the flushing process.

In an alternative set of experiments, the composition of the present invention was used in an aerated lagoon system comprising three lagoons, linked to form a passage to a river, into which lagoons was pumped effluent. Each lagoon had a number of floating aerators thereon. The sewage entered the first lagoon and then flowed through all three lagoons, becoming purified as it flowed, until the effluent flowing to the river met environmental and safety standards.

By adding the composition of the present invention by means of a metering pump it was found that the breakdown of sewage was improved such that several of the aerators were no longer needed and thus a considerable electricity saving was effected. It was further discovered that re-alignment of the aerators to control movement of the water through the lagoons so as to maintain circulation of the water throughout each lagoon improved the digestion of the sewage even further by increasing the biological contact time with the sewage.

Using the composition of the present invention in the three lagoons, a 95.5% removal of BOD5 and an 84.6% removal of total suspended solids was effected.

The recommended doses of the composition of the present invention depends greatly upon the target environment. Because there are many variables that can be considered, such as loading of organic materials, flow rates and energy in the system, there is no specific dose that can be recommended for all circumstances. However it is well within the understanding of a person skilled in the art as to the variables involved and, therefore, the dosage rates that will be required to obtain an acceptable result. In many cases the composition according to the present invention may be applied according to the volume of flow through the target environment and the dynamics present. A high flow through the target environment or high dynamics requires a lower application rate to cause the required effect and the lower the volume of flow/dynamics the greater the required application rate of the composition according to the present invention.

What is claimed is:

1. A method of stimulating the metabolism of a microorganism comprising contacting a microorganism with a bioenhancing composition for the stimulation of a metabolism of a microorganism, which composition comprises a yucca extract, said yucca extract comprising carbohydrate and at least 0.01% by weight of saponin, said yucca extract having a Brix value of approximately 5 to 30, said composition having a pH value in a range suitable for maintaining bacterial life, and thereby stimulating the metabolism of the microorganism.

2. The method according to claim 1 wherein the yucca extract comprises yucca extract obtained from the schidigera species of yucca.

3. The method according to claim 1 wherein said yucca extract has a Brix value of from 10 to 20.

4. The method according to claim 3 wherein said yucca extract has a Brix value of from 15 to 18.

5. The method according to claim 1 wherein the method is for increasing the breakdown of organic waste.

6. The method according to claim 5 wherein the organic waste comprises grease.

7. The method according to claim 6 wherein the organic waste comprises sewage.

* * * * *